US00PP16613P2

(12) United States Plant Patent
Irie

(10) Patent No.: US PP16,613 P2
(45) Date of Patent: Jun. 6, 2006

(54) ***HYDRANGEA* PLANT NAMED 'RIE 09'**

(50) Latin Name: *Hydrangea macrophylla*
Varietal Denomination: RIE 09

(76) Inventor: Ryoji Irie, 3-7 Narutaki Honmachi Ukyoku, Kyoto (JP)

( * ) Notice: Subject to any disclaimer, the term of this patent is extended or adjusted under 35 U.S.C. 154(b) by 111 days.

(21) Appl. No.: 10/986,409

(22) Filed: Nov. 12, 2004

(51) Int. Cl.
*A01H 5/00* (2006.01)

(52) U.S. Cl. ..... Plt./250

(58) Field of Classification Search ..... Plt./250
See application file for complete search history.

*Primary Examiner*—Anne Marie Grunberg
*Assistant Examiner*—Annette H Para

(57) ABSTRACT

A new cultivar of *Hydrangea* plant named 'RIE 09' that is characterized by broad upright habit, large dark grey-green leaves, flowers that range in color from yellow-green to light and dark pink, and unique inflorescence development. In combination these traits set 'RIE 09' apart from all other existing varieties of *Hydrangea* known to the inventor.

3 Drawing Sheets

Genus: *Hydrangea.*
Species: *macrophylla.*
Denomination: RIE 09.

BACKGROUND OF THE INVENTION

The present invention relates to a new and distinct cultivar of *hydrangea* that is grown for use as an indoor floral potted plant and an outdoor ornamental flowering shrub. The new cultivar is known botanically as *Hydrangea macrophylla* and will be referred to hereinafter by the cultivar name 'RIE 09'.

'RIE 09' resulted from a breeding program that was conducted by the inventor at the inventor's nursery in Kyoto, Japan and began in 1990. The purpose of the breeding program was to produce new varieties of floral potted *hydrangeas* that exhibit new and unique flowers and flower color.

Between May 1990 and May 1993 the inventor assembled a collection of unnamed and unreleased hybrids from a sequence of deliberate pollinations involving the following cultivars, all unpatented, and available in commerce in Japan: *Hydrangea macrophylla* 'Otafuku', *Hydrangea macrophylla,* 'Yamaajisai', and *Hydrangea macrophylla* 'Fijinishiritaki'. The inventor did not record which variety was used as male parent and which as female parent. In May 1993, the inventor carried out a deliberate pollination between one unnamed plant from the inventor's collection as female parent and the variety *Hydrangea macrophylla* 'Sumidanohanabi' (unpatented) as male parent.

The pollination described above produced thirty-five individual varieties, which the inventor considered novel and unusual. One of these individual varieties was selected by the inventor in June 1994 and is the subject of the present invention, 'RIE 09'.

'RIE 09' is a deciduous shrub that exhibits large dark grey-green leaves and individual flowers that range in color from yellow-green to light and dark pink. Selection was based on the distinguishing characteristics of flowers, flower color, and inflorescence development. 'Lace cap' type *hydrangeas* produce showy sterile flowers along the outside of the inflorescence, and small inner flowers that are fertile flowers. When an individual inflorescence of 'RIE 09' first opens, it looks like a 'lace cap' type inflorescence with large sterile flowers on the edge. However, unlike the 'lace cap' type *Hydrangea,* the inflorescence eventually fills out completely. Within the inflorescence, center fertile flowers are intermixed with center sterile flowers, so that as the inflorescence develops further, the sterile flowers in the center open fully to then cover the smaller fertile flowers. 'RIE 09' is distinguishable from the parent plants by flower color, and unique inflorescence development, which produces an average of 150 sterile flowers and 400 fertile flowers per inflorescence.

The inventor considers that 'RIE09' is distinct from other varieties of *Hydrangea* known to the inventor in the following respects:

First, whereas other varieties of *Hydrangea* in commerce have four petals per floret on a flat, one-dimensional plane, 'RIE 09' has two to three layers of petals per floret, creating a double-flower appearance.

Second, whereas many novel varieties have been found in, or brought from, Japan in recent years, none appear to have the combination of uniqueness of flower form as above combined with greater vigor and faster growing to flowering stage which typifies 'RIE 09'.

Third, the vigor of 'RIE 09' is evident in its strong thick stems which do not require staking to support the heavy blooms. 'RIE 09', although vigorous, exhibits a shorter internode distance than many other commercial forms of *Hydrangea,* allowing 'RIE 09' to be grown commercially with less or even no application of growth regulating chemical.

'RIE 09' was first asexually propagated by the inventor, in the spring of 1995 in a cultivated area of Kyoto, Japan. The method used for asexual propagation was softwood cuttings. The characteristics of the new *Hydrangea* cultivar named 'RIE 09' have been determined stable and are reproduced true to type in successive generations.

SUMMARY OF THE INVENTION

The following traits have been repeatedly observed and represent the characteristics of the new *Hydrangea* cultivar 'RIE 09'. These traits in combination distinguish 'RIE 09' from all other commercial varieties of *Hydrangea* known to the inventor. 'RIE 09' has not been tested under all possible conditions and phenotypic differences may be observed with variations in environmental, climatic and cultural conditions, without however, any difference in genotype.

1. *Hydrangea* 'RIE 09' is grown for use as both an indoor floral potted plant and an outdoor ornamental flowering shrub.
2. *Hydrangea* 'RIE 09' exhibits individual flowers that range in color from yellow-green to light and dark pink.
3. *Hydrangea* 'RIE 09' exhibits unique inflorescence development that produces an average of 150 sterile flowers and 400 smaller fertile flowers per inflorescence.
4. *Hydrangea* 'RIE 09' exhibits a broad upright habit.
5. *Hydrangea* 'RIE 09' exhibits large dark grey-green leaves.
6. *Hydrangea* 'RIE 09' is 39 cm. in height and 48 cm. in diameter in a 1.5-liter container.
7. *Hydrangea* 'RIE 09' is a shrub.
8. *Hydrangea* 'RIE 09' is deciduous.
9. *Hydrangea* 'RIE 09' performs best when planted in loam based moisture retentive soil, in partial shade, with regular water.
10. *Hydrangea* 'RIE 09' is asexually propagated by the method of softwood cuttings.
11. *Hydrangea* 'RIE 09' exhibits rigid, strong basal branches.
12. *Hydrangea* 'RIE 09' is hardy to USDA Zone 5.
13. *Hydrangea* 'RIE 09' blooms continuously from early April to September.

BRIEF DESCRIPTION OF THE DRAWINGS

The accompanying color drawings illustrate the overall appearance of the new *Hydrangea* cultivar 'RIE 09' showing the colors as true as it is reasonably possible to obtain in colored reproductions of this type. Colors in the photographs may differ from the color values cited in the detailed botanical description, which accurately describe the actual colors of the new variety of *Hydrangea* named 'RIE 09'.

The drawing labeled as FIG. 1 depicts an individual whole plant growing in a 1.5-liter container in a frost-protected greenhouse in De Kwakel, The Netherlands. The plant is approximately twenty one months old. The plant was produced from a cutting which was rooted and grown in a four inch container, then transplanted into the 1.5 liter container, then pinched to encourage basal branching, then allowed to shoot from the base and allowed to flower in its natural season. The plant was pruned back to the base after flowering. The drawing depicts the vigorous basal branching habit of 'RIE 09' in its second season of re-growth. Such a plant would be highly suitable for use as a stock plant for the purpose of providing cutting material for commercial propagation.

Figure 1:
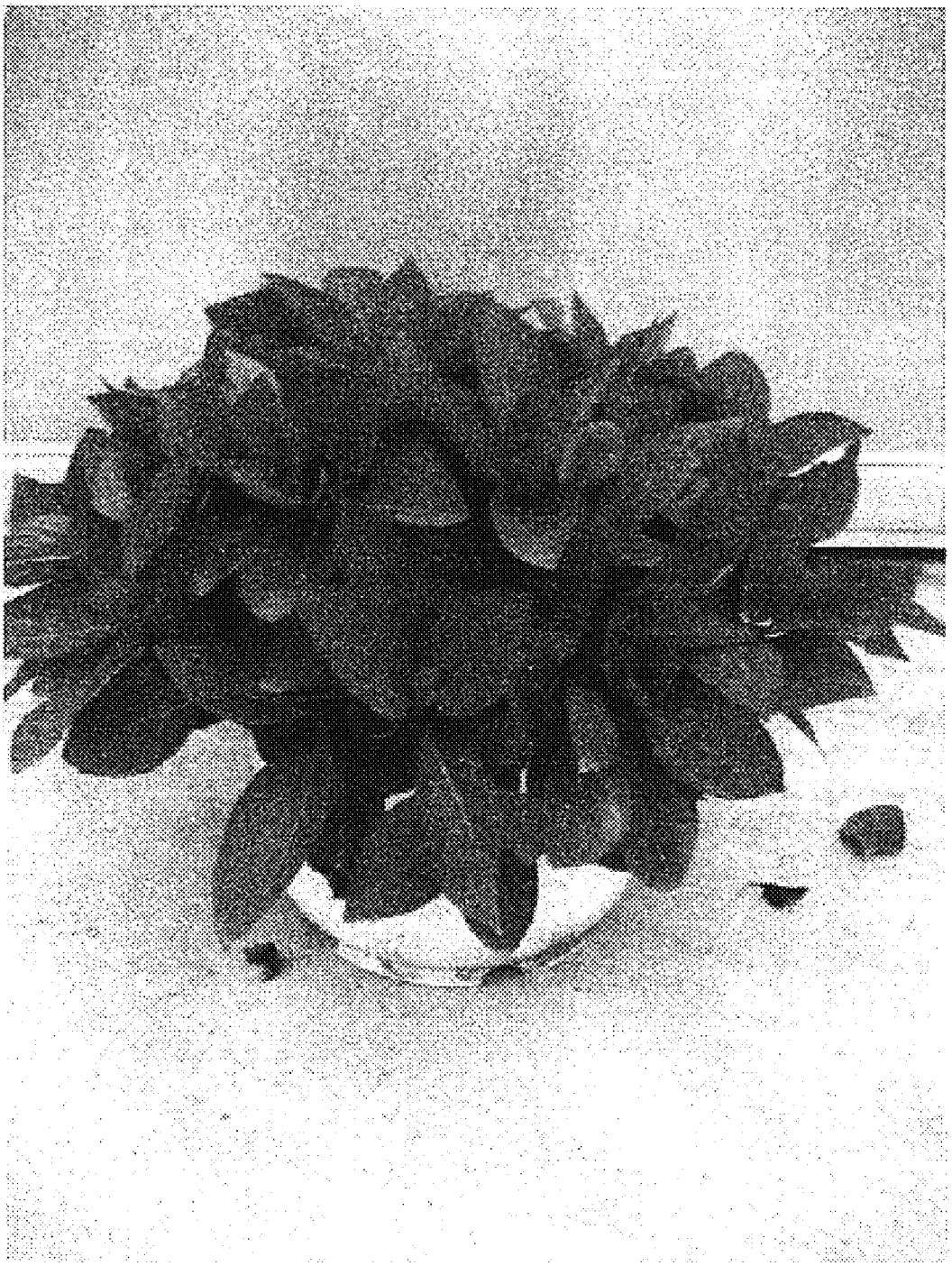
Figure 2:
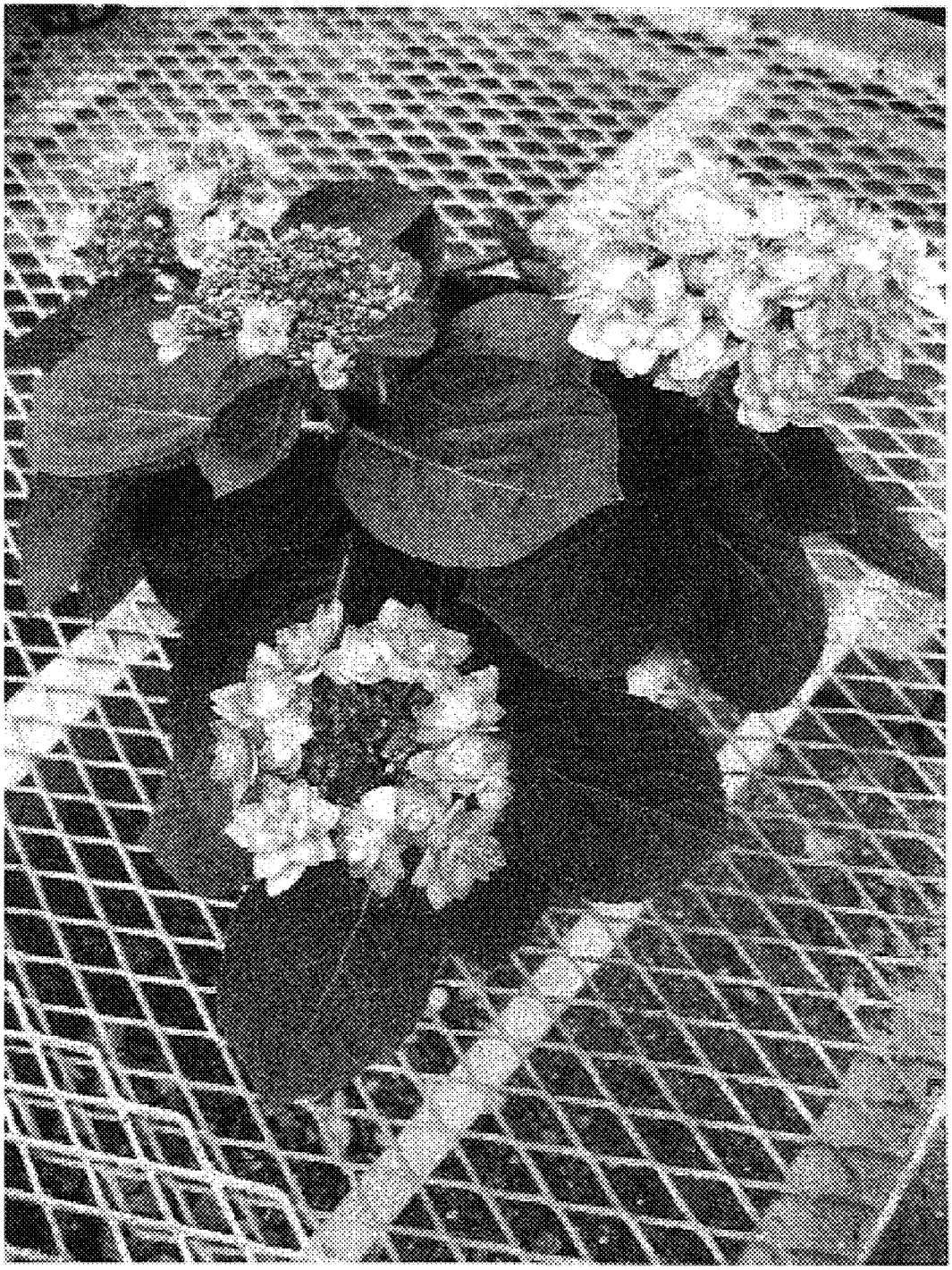

The drawing labeled as FIG. 2 illustrates a one year old plant of 'RIE 09' which has been grown in a 1.5 liter container in a frost-protected greenhouse in De Kwakel, The Netherlands. The plant was produced from a cutting which was rooted and grown in a four inch container, then transplanted into the 1.5 liter container and pinched to encourage basal branching. Three branches arose and were allowed to flower. This drawing depicts the inflorescence of 'RIE 09' at three developmental stages, from first opening of an individual sterile flower to full development of the sterile flowers which are held above, and covering, the smaller fertile flowers.

Figure 3:
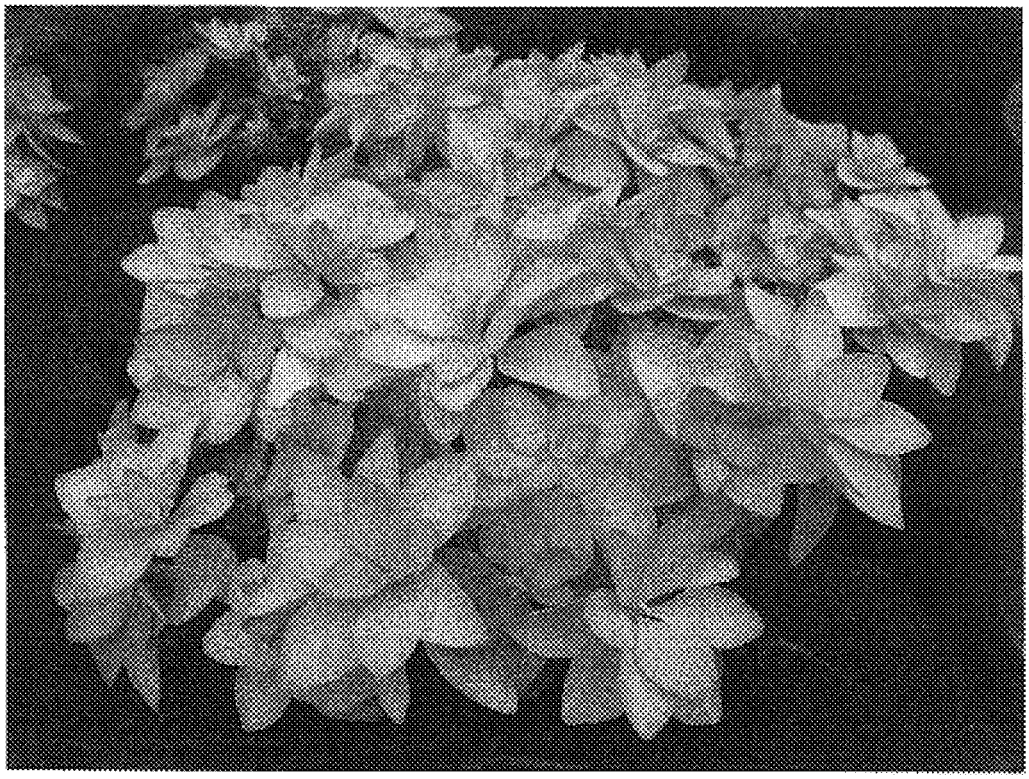

The drawing labeled FIG. 3 illustrates the inflorescence of 'RIE09', in which the center fertile flowers are intermixed with center sterile flowers. This drawing depicts the inflorescence at the stage when the sterile flowers are almost all developed and covering the smaller fertile flowers.

All drawings were made using conventional techniques and although colors may appear different from actual colors due to light reflectance they are as accurate as possible, by conventional photography.

BOTANICAL DESCRIPTION OF THE PLANT

The following is the detailed description of 'RIE 09' as grown in a greenhouse in De Kwakel, The Netherlands. Data was collected in April 2004 from 12-month-old plants grown in 1.5-liter containers. Plants were grown in Peat moss soils with a PH of 6.0 to 6.4. The color determinations are in accordance with the 2002 Edition of the Colour Chart of The Royal Horticultural Society, London, England, except where general color terms of ordinary dictionary significance are used. The growing requirements are similar to the species.

Botanical classification: *Hydrangea macrophylla* 'RIE 09'.
Genus: *Hydrangea.*
Species: *macrophylla.*
Determination: 'RIE 09'.
Commercial classification: Floral plant, ornamental shrub.
Common name: *Hydrangea.*
Use: Grown for use as a potted indoor plant or as an outdoor ornamental flowering shrub.
Container size: Suggested container size is 1.5-liter.
Cultural requirements: Performs best when planted in loam based moisture retentive soil, in partial shade, with regular water.
Parentage: *Hydrangea macrophylla* 'RIE 09' is a hybrid plant that resulted from the induced cross-pollination of the following parent plants:
- *Female parent.*—An unnamed individual *Hydrangea macrophylla.*
- *Male parent.*—An individual *Hydrangea macrophylla* 'Sumidanohanabi' (unpatented).

Plant description:
- *Blooming seasons.*—Spring and summer (natural season) or year-round if forced.
- *Plant habit.*—Broad upright.
- *Plant type.*—Deciduous shrub.
- *Overall plant shape.*—Broad inverted triangle.
- *Vigor.*—Moderate.
- *Growth rate.*—An average of 15-cm. per month in spring.
- *Plant height.*—39 cm. in height.
- *Plant diameter.*—48 cm. in diameter.
- *Hardiness.*—USDA Zone 5.
- *High temperature tolerance.*—Tolerant to 32° Centigrade.
- *Root system.*—Fibrous.
- *Propagation.*—Propagation is accomplished by the method of softwood cuttings.
- *Time and temperatures to develop roots.*—Approximately 4 weeks is needed to develop roots on an initial cutting, at temperatures of 18° to 20° Centigrade.

*Crop time* (*outdoor plant crop*).—An average of 12 months is needed to produce a commercial container size flowering outdoor plant, from a rooted cutting.

*Temperatures* (*outdoor plant crop*).—From rooted cuttings to commercial size containers, the outdoor crop is grown at natural outdoor temperatures utilizing unheated greenhouses for winter protection.

*Crop time* (*indoor plant crop*).—An average of 4–6 months is needed to produce a commercial container size flowering indoor plant, from a rooted cutting.

*Temperatures* (*indoor plant crop*).—Transplant rooted cuttings to liner pots and keep for a minimum of 6 weeks at below 5° Centigrade to force dormancy. Transplant to 1.5-liter containers and keep at 18° to 25° Centigrade for a minimum or 10 weeks to produce commercial container size flowering plants.

*Disease and pest resistance or susceptibility.*—No susceptibility to pests or disease known to the inventor.

Stem:

*Number of lateral branches.*—An average of 3 lateral branches.

*Lateral branch length.*—Average is 27 cm. in length.

*Lateral branch diameter.*—Average is 5 mm. in diameter.

*Stem shape.*—Cylindrical.

*Stem surface.*—Slightly glossy.

*Pubescence.*—None observed.

*Stem strength.*—Strong.

*Stem texture.*—Rigid.

*Stem color.*—Individual colors 144A, 144B, N186B and N186C are present on an individual stem.

*Lenticles.*—Present.

*Quantity of lenticels.*—An average of 8 per cubic cm. of stem surface.

*Lenticel color.*—A combination of colors N186B and N186C is present on an individual lenticel.

*Lenticel height.*—An average of 0.5 mm. in height.

*Lenticel width.*—An average of 2.5 mm. in width.

*Branching habit.*—Moderate to sparse basal branching.

*Branching requirements.*—Pinching encourages lateral branching.

*Internode length.*—5.9 cm. between nodes.

Foliage:

*Type.*—Deciduous.

*Arrangement.*—Opposite.

*Division.*—Simple.

*Quantity of leaves per lateral stem.*—An average of 10 individual leaves per lateral stem.

*Leaf shape.*—Leaves range from oval to elliptic-oblong on an individual plant.

*Apex.*—Short apiculate.

*Base.*—Leaf base ranges from obtuse to short attenuate on an individual plant.

*Leaf margins.*—Crenate.

*Leaf length.*—Average is 15 cm. in length.

*Leaf width.*—Average is 11.1 cm. in width.

*Leaf appearance* (*adaxial and abaxial surfaces*).—Semi-glossy surfaces.

*Leaf surfaces* (*adaxial and abaxial surfaces*).—Glabrous.

*Pubescence.*—None present.

*Venation pattern.*—Pinnate.

*Vein color* (*abaxial surfaces*).—147C.

*Vein color* (*adaxial surfaces*).—147C.

*Leaf color* (*adaxial surfaces*).—A combination of colors 139A and N189A is present on an individual leaf.

*Leaf color* (*abaxial surfaces*).—A combination of colors 137B and 137C is present on an individual leaf.

*Attachment.*—Petiolate.

*Petiole length.*—An average of 3.2 cm. in length.

*Petiole diameter.*—An average of 3 mm. in diameter.

*Petiole surface.*—Glabrous.

*Petiole shape.*—Cylindrical.

*Petiole color.*—144A.

*Durability of foliage to stress.*—High durability to stress.

*Stipules, tendrils, thorns.*—None observed.

*Fragrance.*—None observed.

Flowers:

*Flower arrangement.*—Terminal inflorescence.

*Inflorescence type.*—Compound corymb.

*Inflorescence height.*—An average of 12 cm. in height.

*Inflorescence diameter.*—An average of 23.6 cm. in diameter.

*Quantity of flowers per inflorescence.*—An average of 400 fertile flowers and 150 sterile flowers per individual inflorescence.

*Flowering habit.*—An individual plant blooms continuously from early April September.

*Quantity of flowers per lateral stem.*—An average of 400 fertile flowers, and 150 sterile flowers per individual lateral stem.

*Quantity of flower buds per lateral stem.*—An average of 400 fertile flower buds and 150 sterile flower buds per individual lateral stem.

*Quantity of flowers and buds per plant.*—An average of 800 fertile buds and flowers, and an average of 300 sterile buds and flowers per individual plant.

*Bud length.*—Fertile flower buds are an average of 3 mm. in length and sterile flower buds are an average of 6 mm. in length.

*Bud diameter.*—Fertile flower buds are an average of 2 mm. in diameter and sterile flower buds are an average of 4 mm. in diameter.

*Bud shape* (*fertile and sterile buds*).—Obovate.

*Bud apex* (*fertile and sterile buds*).—Obtuse.

*Bud color* (*fertile and sterile buds*).—144A.

*Flower aspect* (*fertile flowers*).—Flowers range from upward to outward facing on an individual plant.

*Flower aspect* (*sterile flowers*).—Sterile flowers are slightly drooping.

*Rate of opening* (*fertile and sterile flowers*).—An average of 10% of the flowers on an individual plant open at once, and all the flowers on an individual plant have opened by 6 weeks.

*Flower diameter.*—Fertile flowers are an average of 2.5 cm. in diameter, and sterile flowers are an average of 5.7 cm. in diameter.

*Flower depth.*—Fertile flowers are an average of 5 mm. in depth and sterile flowers are an average of 2.1 cm. in depth.

*Flower shape* (*fertile and sterile flowers*).—Rotate in shape.

*Persistent or self-cleaning* (*fertile and sterile flowers*).—Persistent.

*Peduncle shape.*—Cylindrical.

*Peduncle color.*—Individual colors 144B and N186B are present on an individual peduncle.

*Peduncle length.*—Average is 10.6 cm. in length.

*Peduncle diameter.*—Average is 3 mm. in diameter.

*Peduncle surface.*—Puberulent.

*Peduncle angle.*—Average angle is 40°.

*Peduncle strength.*—Strong.
*Lenticels.*—Present on peduncle.
*Lenticel color.*—N186B.
*Lenticel height.*—0.75 mm. in height.
*Lenticel width.*—2 mm. in width.
*Pedicels* (*on fertile and sterile flowers*).—Present.
*Lastingness of flowers.*—An individual flower lasts 4 weeks.
*Flower response time.*—An average of 9 weeks.
*Flower fragrance.*—None observed.
*Fertile flowers.*—Petal appearance: Dull. Petal surface: Glabrous. Petal number: An average of 5 petals per flower. Petal fused or unfused: Unfused Petal shape: Elliptic. Petal margin: Entire. Petal apex: Obtuse. Petal length: Average is 2 mm. in length. Petal width: Average is 1 mm. in width. Petal color (abaxial surfaces when opening): 144A. Petal color (adaxial surfaces when opening): 144A. Petal color (abaxial surfaces when fully opened): 144A. Petal color (adaxial surfaces when fully opened): 144A. Calyx: Present. Calyx shape: Campanulate. Calyx length: Average of 2 mm. in length. Calyx diameter: Average of 3 mm. in diameter. Sepals: 5 in number. Fused or unfused: Fused. Sepal shape: Sepals range from ovate to elliptic in shape on an individual inflorescence. Sepal margin: Entire. Sepal apex: Acute. Sepal base: Cuneate. Sepal appearance: Dull. Sepal surfaces (adaxial and abaxial surfaces): Puberulent. Sepal length: Average of 1 mm. in length. Sepal width: Average of 0.8 mm. in width. Sepal color (abaxial and adaxial surfaces): 143B. Pedicel length: Average is 2 mm. in length. Pedicel diameter: Average is 1 mm. in diameter. Pedicel angle: Average angle is 35°. Pedicel strength: Moderate. Pedicel color: A combination of colors 144A and 144B is present on an individual pedicel. Pedicel surface: Puberulent. Lenticels: None observed on pedicels of fertile flowers.
*Sterile flowers.*—Tepal appearance: Dull. Tepal surface: Glabrous. Tepal number: An average of 14 tepals per sterile flower. Tepals fused or unfused: Unfused. Tepal shape: Sepals range from broad elliptic to rhomboidal on an individual inflorescence. Tepal margin: Entire. Tepal apex: Closest to rounded. Tepal length: Tepals range from 9 mm. to 2.4 cm. in length on an individual plant. Tepal width: Tepals range from 5 mm. to 1.8 cm. in width. Tepal color (abaxial surfaces when opening): 69D. Tepal color (adaxial surfaces when opening): 75C. Tepal color (abaxial surfaces when fully opened): 75D. Tepal color (adaxial surfaces when fully opened): 76B. Tepal color fading to (adaxial and abaxial surfaces): A combination of colors 145D and 75D. Calyx: None observed. Pedicel length: Average is 3 cm. in length. Pedicel diameter: Average is 2 mm. in diameter. Pedicel angle: Average angle is 45°. Pedicel strength: Moderate. Pedicel color: A combination of colors 75B and 75C. Pedicel surface: Glabrous. Pubescence: None observed. Lenticels: None observed.

Reproductive organs:
*Stamens.*—None observed.
*Anthers.*—None observed.
*Pistil.*—Present.
*Pistil number.*—An average of 4 present per individual fertile flower.
*Pistil length.*—An average of 2 mm. in length.
*Stigma.*—Present.
*Stigma shape.*—Clavate.
*Stigma color.*—155A.
*Style length.*—An average of 1.5 mm. in length.
*Style color.*—A combination of colors 144B and 144C.
*Ovary.*—Present on fertile flowers.
*Ovary position.*—Inferior.
*Ovary color.*—157D.
*Ovary dimensions.*—0.2 mm. in height and 0.2 mm. in diameter.
*Ovary shape.*—Globular.

Seed production: No seed production has been observed to date.

What is claimed is:

1. A new and distinct cultivar of *Hydrangea* plant named 'RIE 09' as described and illustrated herein.

* * * * *